United States Patent
Anderson

(10) Patent No.: US 11,932,750 B2
(45) Date of Patent: Mar. 19, 2024

(54) RESIN BLENDS INCLUDING PHTHALONITRILE RESIN AND THIADIAZOLE SUBSTITUTED PHTHALONITRILE COMPOUND, ARTICLES, COMPOUNDS, AND METHODS

(71) Applicant: 3M INNOVATIVE PROPERTIES COMPANY, St. Paul, MN (US)

(72) Inventor: Benjamin J. Anderson, Eden Prairie, MN (US)

(73) Assignee: 3M Innovative Properties Company, St. Paul, MN (US)

(*) Notice: Subject to any disclaimer, the term of this patent is extended or adjusted under 35 U.S.C. 154(b) by 508 days.

(21) Appl. No.: 17/283,092

(22) PCT Filed: Nov. 13, 2019

(86) PCT No.: PCT/IB2019/059763
§ 371 (c)(1),
(2) Date: Apr. 6, 2021

(87) PCT Pub. No.: WO2020/109902
PCT Pub. Date: Jun. 4, 2020

(65) Prior Publication Data
US 2021/0340355 A1 Nov. 4, 2021

Related U.S. Application Data

(60) Provisional application No. 62/773,244, filed on Nov. 30, 2018.

(51) Int. Cl.
C08K 5/47 (2006.01)
C07D 285/125 (2006.01)
C08K 3/26 (2006.01)

(52) U.S. Cl.
CPC .......... *C08K 5/47* (2013.01); *C07D 285/125* (2013.01); *C08K 3/26* (2013.01)

(58) Field of Classification Search
CPC ......... C08K 5/47; C08K 3/26; C07D 285/125
USPC ........................................................ 524/83
See application file for complete search history.

(56) References Cited

U.S. PATENT DOCUMENTS

| 3,496,250 A | 2/1970 | Czerwinski |
| 4,097,669 A | 6/1978 | Reisdorff |
| 4,223,123 A | 9/1980 | Keller |
| 4,304,896 A | 12/1981 | Keller |
| 4,408,035 A | 10/1983 | Keller |

FOREIGN PATENT DOCUMENTS

| WO | WO 2017-172515 | 10/2017 |
| WO | WO 2017-173040 | 10/2017 |
| WO | WO 2017-173195 | 10/2017 |

OTHER PUBLICATIONS

Debirgas et al., Spectrochimica Acta Part A: Molecular and Biomolecular Spectroscopy, 153, 71-78, 2016. (Year: 2016).*
Demirbas, "Electrochemical and spectroelectrochemical properties of thiadiazole substituted metallo-phthalocyanines", Spectrochimica Acta Part A: Molecular and Biomolecular Spectroscopy, Jan. 2016, vol. 153, pp. 71-78.
Dominguez, "Properties of phthalonitrile monomer blends and thermosetting phthalonitrile copolymers", Polymer, 2007, vol. 48, No. 1, pp. 91-97.
Guzel, "Synthesis and photophysicochemical properties of novel thiadiazole-substituted zinc(II), gallium (III) and silicon (IV) phthalocyanines for photodynamic therapy", Inorganica Chimica Acta, Oct. 2017, vol. 467, pp. 169-176.
Hu, "1,3,4-Thiadiazole: Synthesis, Reactions, and Applications in Medicinal, Agricultural, and Materials Chemistry", Chemical Reviews, Apr. 2014, vol. 114, No. 10, pp. 5572-5610.
Islyaikin, "Thiadiazole-Derived Expanded Heteroazaporphyrinoids", Organic Letters, 2001, Vo. 3, No. 14, pp. 2153-2156.
McKeown, The Porphyrin Handbook, 61-124 (2003).
International Search Report for PCT International Application No. PCT/IB2019/059763, dated Jan. 28, 2020, 3 pages.

* cited by examiner

*Primary Examiner* — Hui H Chin
(74) *Attorney, Agent, or Firm* — Adrian L. Pishko

(57) ABSTRACT

The present disclosure provides a resin blend containing a blend of a phthalonitrile resin and a thiadiazole substituted phthalonitrile compound. The present disclosure also provides an article including a polymerization product of such a resin blend. Further, a thiadiazole substituted phthalonitrile compound and an article including a polymerization product of the compound are provided. The present disclosure additionally provides a method of making a thiadiazole substituted phthalonitrile compound. Certain thiadiazole substituted phthalonitrile compounds can act as curatives for the phthalonitrile resin.

15 Claims, No Drawings

RESIN BLENDS INCLUDING PHTHALONITRILE RESIN AND THIADIAZOLE SUBSTITUTED PHTHALONITRILE COMPOUND, ARTICLES, COMPOUNDS, AND METHODS

FIELD

The present disclosure generally relates to phthalonitrile resin blends and thiadiazole substituted phthalonitrile compounds.

BACKGROUND

Phthalonitriles are dinitrile ortho substituted aromatic rings. Phthalonitriles and their ring substituted variants are important precursors in the development of chemical dyes, pigments, and agrochemicals. Of more recent interest, phthalonitrile (PN) resins are being developed for use in emerging fields such as electronic materials, energy storage, and structural materials. Phthalonitriles will oligomerize and cyclize under various documented reaction conditions. (McKeown, N. B., *The Synthesis of Symmetrical Phthalocyanines*, in *The Porphyrin Handbook*, K. M. Kadish, K. M. Smith, and R. Guilard, Editors. 2003, Academic Press: Amsterdam. p. 61-124.)

Thiadiazoles are aromatic heterocycles containing a sulfur atom and two nitrogen atoms. There are several thiadiazole isomeric variants: 1,2,3-thiadiazole, 1,2,4-thiadiazole, 1,2,5-thiadiazole, 1,3,4-thiadiazole. Thiadiazoles are utilized in nature and synthetically as a molecular structural component of various bioactive agents. Medicinal drugs based on thiadiazole demonstrate antimicrobial activity, specifically antitubercular, antiviral, anti-inflammatory, antitumor, analgesic, antiepileptic, and other activities. (Hu, Y., et al., *1,3,4-Thiadiazole: Synthesis, Reactions, and Applications in Medicinal, Agricultural, and Materials Chemistry*. Chemical Reviews, 2014. 114(10): p. 5572-5610.) Therefore, thiadiazoles have broad pharmacological significance.

SUMMARY

Resin blends containing phthalonitrile resins and thiadiazole substituted phthalonitrile compounds are described. The resin blends provide good processing (i.e., low melt temperature, wide processing temperature window) and polymer network formation (i.e., low polymerization temperature, out-of-autoclave polymerization reaction, low network glass transition temperature) of phthalonitrile resins containing thiadiazole functionality.

In a first aspect, a resin blend is provided. The resin blend includes at least one phthalonitrile resin and a compound of Formula I:

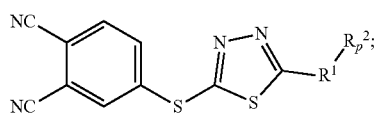

wherein p is 0 or 1. When p is 0, $R^1$ is H, an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH(=O), —S—$R^3$, —C(=O)—N—$R_2^4$, —S($O_2$)—$R^5$, a carboxylic acid group, or a halogen, wherein $R^3$ is an alkyl group, each $R^4$ is independently H or an alkyl group, and $R^5$ is H or an alkyl group. When p is 1, $R^1$ is a covalent bond, an arylene group, or an aralkylene group; and $R^2$ is an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH(=O), —S—$R^3$, —C(=O)—N—$R_2^4$, —S($O_2$)—$R^5$, a carboxylic acid group, or a halogen, wherein $R^3$ is an alkyl group, each $R^4$ is independently H or an alkyl group, and $R^5$ is H or an alkyl group.

In a second aspect, an article is provided. The article includes a polymerization product of the resin blend of the first aspect.

In a third aspect, a compound is provided. The compound is of Formula II:

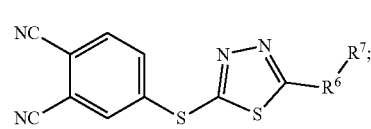

wherein $R^6$ is a covalent bond, an arylene group, or an aralkylene group; and $R^7$ is a hydroxyl group, a thiol group, —S—$R^8$, wherein $R^8$ is an alkyl group, or an amino group.

In a fourth aspect, another article is provided. The article includes a polymerized reaction product of the compound of Formula II according to the third aspect.

In a fifth aspect, a method of making a compound of Formula II is provided:

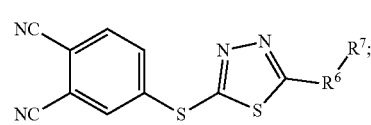

wherein $R^6$ is a covalent bond, an arylene group, or an aralkylene group; and $R^7$ is a hydroxyl group, a thiol group, —S—$R^8$, wherein $R^8$ is an alkyl group, or an amino group. The method includes a) combining components to form a mixture, and b) reacting the mixture with stirring. The components include:
  i) 4-nitrophthalonitrile;
  ii) a compound of Formula III:

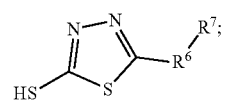

wherein $R^6$ and $R^7$ are as defined for Formula II;
  iii) an aprotic solvent; and
  iv) a base.

Temperature resistant polymer networks are critical for an increasing number of market applications. As the environmental temperature of an application increases, the number of available materials able to meet requirements shrinks rapidly. The present resin blends containing thiadiazole substituted phthalonitrile compounds as additives and/or curatives are useful for applications in which a temperature resistant polymer is beneficial, particularly applications in which thiadiazole functionality is beneficial.

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example "A and/or B" means only A, only B, or both A and B.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

As used herein, the term "phthalonitrile" is inclusive of compounds having the characteristic benzene derivative having two adjacent nitrile groups. In the illustrated phthalonitrile group, R is for instance and without limitation, ether, thioether, aryl, alkyl, halogen, amine, ester, or amide, heteroalkyl, or (hetero)hydrocarbyl.

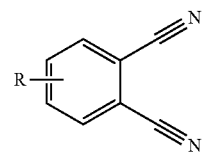

As used herein, "bisphenol M diphthalonitrile ether" refers to bis(3,4-dicyanophenyl) ether of bisphenol M.

As used herein, "bisphenol T diphthalonitrile ether" refers to bis(3,4-dicyanophenyl) ether of bisphenol T.

As used herein, "bisphenol P diphthalonitrile ether" refers to bis(3,4-dicyanophenyl) ether of bisphenol P.

As used herein, "resorcinol diphthalonitrile ether" refers to bis(3,4-dicyanophenyl) ether of resorcinol.

As used herein, the term "thiadiazole" is inclusive of aromatic heterocycles containing a sulfur atom and two nitrogen atoms. For instance, the arrangement of sulfur and nitrogen atoms provide the following isomeric variants: 1,2,3-thiadiazole, 1,2,4-thiadiazole, 1,2,5-thiadiazole, and 1,3,4-thiadiazole.

As used herein, "thiadiazole substituted phthalonitrile compound" refers to a compound in which a thiadiazole group is attached to a phthalonitrile molecule through a sulfide linkage between the second carbon of the thiadiazole ring and the third or fourth carbon of the phthalonitrile molecule.

As used herein, a "particle" has an aspect ratio of less than 50:1 of the largest dimension to the smallest dimension, and excludes fibers. As used herein, "nanoparticle" refers to a particle having a D90 particle diameter below 1 micrometer (e.g., "submicron"). As used herein, "particle diameter" refers to the largest dimension of a particle. A suitable method to determine the particle diameter of a nanometer scale particle includes transmission electron microscopy (TEM). As used herein, "microparticle" refers to a particle having a D90 particle diameter below 1 millimeter. A suitable method to determine the particle diameter of a micrometer scale particle includes dynamic light scattering. As used herein, "D90" refers to 90 percent of a population of particles having a particle diameter below the particular particle diameter value.

As used herein, "nanofiller" refers to an additive included in a resin blend that has at least two dimensions (of height, width, and length) that are less than 1 micrometer. As used herein, "microfiller" refers to an additive included in a resin blend that has at least two dimensions (of height, width, and length) that are less than 1 millimeter.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, Si, P, and N, and both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, the term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

As used herein, the term "aralkylene" refers to a divalent group of formula —R—Ar$^a$— where R is an alkylene and Ar$^a$ is an arylene (i.e., an alkylene is bonded to an arylene).

As used herein, the term "alkoxy" refers to a monovalent group of formula —OR, where R is an alkyl group.

As used herein, the term "carbonyl" refers to a divalent group of formula —(CO)—, where the carbon atom is attached to the oxygen atom with a double bond.

As used herein, the term "alkoxycarbonyl" refers to a monovalent group of formula —C(=O)OR, where R is an alkyl group.

As used herein, the term "alkylcarbonyl" refers to a monovalent group of formula —(CO)R, where the carbon atom is attached to the oxygen atom with a double bond and where R is an alkyl group.

As used herein, "(hetero)hydrocarbyl" is inclusive of (hetero)hydrocarbyl alkyl and aryl groups, and hetero(hetero)hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero)hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

As used herein, the term "thienyl" refers to a monovalent group having the formula

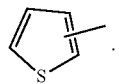

As used herein, the term "hydroxyl" refers to a monovalent group of formula —OH.

As used herein, the term "thiol" refers to a monovalent group of formula —SH.

As used herein, the term "amino" refers to a monovalent group of formula —NR$_2$, where each R is independently H or an alkyl.

As used herein, the term "carboxylic acid" refers to a monovalent group of formula —C(=O)OH.

As used herein, the term "halogen" refers to an atom selected from fluorine, chlorine, bromine, or iodine.

As used herein, the term "polymerized product" refers to a polymerized result of a polymerization reaction of a polymerizable composition.

As used herein, the term "residue" is used to define the (hetero)hydrocarbyl portion of a group remaining after removal (or reaction) of the attached functional groups, or the attached groups in a depicted formula. For example, the "residue" of butyraldehyde, C$_4$H$_9$—CHO is the monovalent alkyl C$_4$H$_9$—. The residue of phenylene diamine H$_2$N—C$_6$H$_4$—NH$_2$, is the divalent aryl —C$_6$H$_4$—.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

The present disclosure is generally directed to resin blends, thiadiazole substituted phthalonitrile compound, articles, and methods. This disclosure provides a 1,3,4-thiadiazole moiety coupled to a phthalonitrile moiety to create a diverse set of thiadiazole based (e.g., substituted) phthalonitrile molecules and resins. The coupling of the thiadiazole with the phthalonitrile offers a means to coupling the unique activity of the thiadiazole with the diverse chemistry of the phthalonitrile and may find use in chemical pigments and dyes, agrochemicals, and medicinal agents. Recent work in the development and polymerization of phthalonitriles offers a direct means of incorporating thiadiazoles in polymer networks.

In a first aspect, a resin blend is provided. The resin blend comprises a blend of a (e.g., at least one) phthalonitrile resin and a compound of Formula I:

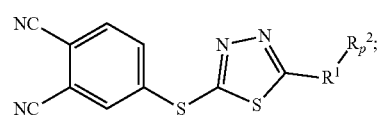

wherein p is 0 or 1;
when p is 0, R$^1$ is H, an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH(=O), —S—R$^3$, —C(=O)—N—R$_2^4$, —S(O$_2$)—R$^5$, a carboxylic acid group, or a halogen, wherein R$^3$ is an alkyl group, each R$^4$ is independently H or an alkyl group, and R$^5$ is H or an alkyl group; and
when p is 1, R$^1$ is a covalent bond, an arylene group, or an aralkylene group, and R$^2$ is an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH(=O), —S—$R^3$, —C(=O)—N—$R_2^4$, —S($O_2$)—$R^5$, a carboxylic acid group, or a halogen, wherein $R^3$ is an alkyl group, each $R^4$ is independently H or an alkyl group, and $R^5$ is H or an alkyl group.

More particularly, when p is 0, in some embodiments $R^1$ is H, an alkyl group, an aryl group, a heteroalkyl group, or a heteroaryl group. In select embodiments, $R^1$ is a heteroalkyl group, wherein the heteroatom is S or N. In some embodiments, $R^1$ is a thienyl group, a thiol group, or —S($O_2$)—$R^5$. In some embodiments, $R^1$ is an alkoxy group, an alkoxycarbonyl group, or an alkylcarbonyl group. In some embodiments, $R^1$ is a hydroxyl group, —CH(=O), —C(=O)—N—$R_2^4$, a carboxylic acid group, or a halogen. In select embodiments, $R^1$ is an amino group. The R groups are as defined above for Formula I.

In select embodiments, p is 0 and $R^1$ is H, an alkyl group, a heteroalkyl group, or an amino group. In certain embodiments, p is 0 and $R^1$ is an amino group. In certain embodiments, p is 0 and $R^1$ is methyl. In certain embodiments, p is 0 and $R^1$ is —S—$CH_3$. In certain embodiments, p is 0 and $R^1$ is H.

When p is 1, in some embodiments, $R^1$ is a covalent bond, an arylene group, or an aralkylene group. In select embodiments, $R^1$ is an arylene group. In certain embodiments, $R^1$ is a covalent bond. In some embodiments, $R^2$ is H, an alkyl group, an aryl group, a heteroalkyl group, or a heteroaryl group. In select embodiments, $R^2$ is a heteroalkyl group, wherein the heteroatom is S or N. In some embodiments, $R^2$ is a thienyl group, a thiol group, or —S($O_2$)—$R^5$. In some embodiments, $R^2$ is an alkoxy group, an alkoxycarbonyl group or an alkylcarbonyl group. In some embodiments, $R^2$ is a hydroxyl group, —CH(=O), —C(=O)—N—$R_2^4$, a carboxylic acid group, or a halogen. In select embodiments, $R^2$ is an amino group, a hydroxyl group, or a thiol group, which are each able to react with the phthalonitrile moiety. The R groups are as defined above for Formula I.

The amount of the compound of Formula I is not particularly limited. Typically, the compound of Formula I is present in an amount of 1 weight percent (wt. %) or greater, based on the total weight of the (e.g., one or more) phthalonitrile resin(s), 2 wt. % or greater, 3 wt. % or greater, 5 wt. % or greater, 7 wt. % or greater, 8 wt. % or greater, 10 wt. % or greater, 12 wt. % or greater, 14 wt. % or greater, 16 wt. % or greater, 18 wt. % or greater, 20 wt. % or greater, 22 wt. % or greater, or 24 wt. % or greater; and 70 wt. % or less, 65 wt. % or less, 60 wt. % or less, 55 wt. % or less, 50 wt. % or less, 45 wt. % or less, 40 wt. % or less, 35 wt. % or less, 30 wt. % or less, or 25 wt. % or less, based on the total weight of the phthalonitrile resin(s). In some embodiments, the compound of Formula I is present in an amount of 1 to 70 wt. %, 1 to 20 wt. %, 10 to 20 wt. %, or 20 to 70 wt. %, based on the total weight of the phthalonitrile resin(s).

In a second aspect, an article is provided. The article comprises a polymerization product of the resin blend according to any embodiment of the first aspect. Preferably, the article exhibits a glass transition temperature between 200 and 350 degrees Celsius.

In a third aspect, compound of Formula II is provided:

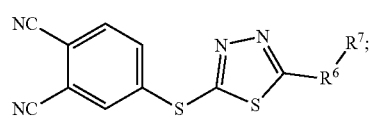

wherein $R^6$ is a covalent bond, an arylene group, or an aralkylene group, and $R^7$ is a hydroxyl group, a thiol group, —S—$R^8$, wherein $R^8$ is an alkyl group, or an amino group.

In select embodiments, $R^6$ is a covalent bond. In some embodiments, $R^6$ is an arylene group that is a phenylene group or an aralkylene group comprising a phenylene group. In select embodiments, $R^7$ is an amino group. In some embodiments, $R^7$ is a hydroxyl group. In some embodiments, $R^7$ is —S—$CH_3$. It has unexpectedly been discovered that reactive functional groups such as amino groups, hydroxyl groups, and thiol groups are able to be employed in the compound of Formula II (e.g., a thiadiazole substituted phthalonitrile) without reacting with the nitrile groups of the phthalonitrile during preparation of the compound of Formula II.

In a fourth aspect, an article is provided. The article comprises a polymerization product of the compound of Formula II according to any embodiment of the second aspect.

Thiadiazole substituted phthalonitrile compounds according to the present disclosure were synthesized by nucleophilic substitution of a nitro group on the third or fourth carbon of the phthalonitrile aromatic ring by 1,3,4-thiadiazole-2-thiolate. The nucleophilic substitution can also be performed with a halogen on the third or fourth carbon of the phthalonitrile aromatic ring. The substitution reaction is accomplished in an aprotic solvent, preferably a polar aprotic solvent. In some embodiments, the aprotic solvent is selected from dimethylsulfoxide (DMSO), dimethyl formamide (DMF), dimethylacetamide (DMAc), N-methylpyrrolidone (NMP), hexamethylphosphoramide (HMPA), tetrahydrofuran (THF), or any combination thereof. In certain embodiments, the aprotic solvent is DMSO. In certain embodiments, the aprotic solvent is DMF.

The thiolate is generated by the addition of a base. In some embodiments, the base is selected from triethylamine, tributylamine, potassium carbonate, sodium carbonate, potassium hydroxide, sodium hydroxide, 1,4-diazabicyclo[2.2.2]octane (DABCO), pyridine, or any combination thereof. In certain embodiments, the base is triethylamine. In certain embodiments, the base is tributylamine. In certain embodiments, the base is potassium carbonate.

Accordingly, in a fourth aspect, a method of making a thiadiazole substituted phthalonitrile compound (e.g., a compound of Formula II) is provided. The method comprises combining components to form a mixture and reacting the mixture with stirring. The components comprise 4-nitrophthalonitrile, a compound of Formula III, an aprotic solvent, and a base.

The compound of Formula II is as follows:

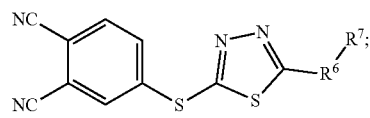

wherein R⁶ is a covalent bond, an arylene group, or an aralkylene group, and R⁷ is a hydroxyl group, a thiol group, —S—R⁸, wherein R⁸ is an alkyl group, or an amino group.

The compound of Formula III is as follows:

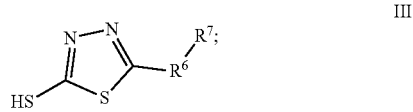

III wherein R⁶ and R⁷ are as defined above for Formula II.

Optionally, the method further comprises adding molecular sieves to the reaction mixture to remove moisture from the mixture during reaction of the components.

Advantageously, the mixture can be reacted for a relatively short amount of time to produce a thiadiazole substituted phthalonitrile compound. In some embodiments, the reaction time is 50 hours or less, 48 hours or less, 42 hours or less, 36 hours or less, 30 hours or less, 24 hours or less, 20 hours or less, 18 hours or less, 16 hours or less, 14 hours or less, 12 hours or less, 10 hours or less, 8 hours or less, 6 hours or less, 5 hours or less, 4 hours or less, 3 hours or less, or 2 hours or less; and 1 hour or more, 2 hours or more, 3 hours or more, 5 hours or more, 10 hours or more, or 12 hours or more; for instance 1 to 20 hours, 1 to 4 hours, or 12 to 16 hours. Moreover, in certain embodiments, the reaction can occur at ambient temperature, ambient pressure, or both. Optionally, the method further includes heating the mixture, cooling the mixture, or both (e.g., at different points during the course of the reaction).

In some embodiments, the method further comprises precipitating the compound of Formula II from the reaction mixture in a blend of water and alcohol. For instance, a blend of methanol and water may be used (e.g., 60/40 to 70/30 by mass of methanol/water).

Different thiadiazole substituted phthalonitrile compounds can be prepared by varying the chemical substituent on the fifth carbon of the thiadiazole ring. In one embodiment, the fifth carbon substituent is a hydrogen. The resulting compound is 4-S-(1,3,4-thiadiazole-2-mercapto)phthalonitrile. In another embodiment, the substituent is a methylmercapto. The resulting compound is 4-S-(5-methylmercapto-1,3,4-thiadiazole-2-mercapto)phthalonitrile. In still another embodiment, when the substitute off of the fifth carbon of the thiadiazole is a methyl group, as demonstrated by 4-(5-methyl-1,3,4-thiadiazole-2-mercapto)phthalonitrile, the thiadiazole coupled phthalonitrile has a melt temperature of 142° C. Upon melting of each of the three aforementioned compounds, the thiadiazole phthalonitriles have each been shown to be stable at elevated temperature (i.e., measured up to 200° C.) and do not show evidence of phthalonitrile oligomerization, as measured by differential scanning calorimetry (DSC), nuclear magnetic resonance (NMR) spectroscopy and infrared (IR) spectroscopy.

In an embodiment when the substitute off of the fifth carbon of the thiadiazole is an amine as demonstrated by 4-S-(5-amino-1,3,4-thiadiazole-2-mercapto)phthalonitrile, the thiadiazole coupled phthalonitrile has a melt temperature of 185° C. Upon melting, the 5-amino substituted thiadiazole demonstrates reactivity with the phthalonitrile, as evidenced by the generation of an exotherm measured by DSC, to form a 1-amino-3-iminoisoindoline. The amine of the thiadiazole attacks the carbon of one of the ortho nitrile groups. The nitrogen of the nitrile group attacks the carbon of the adjacent nitrile group, leading to the formation of a 1-amino-3-iminoisoindolenine. The amine and phthalonitrile dual functionality leads to the formation of a polymer network. The initial exotherm terminates due to vitrification of the forming network. Higher temperatures soften the network and generate a second exotherm believed to be due to continued reaction of the amines and phthalonitrile. The polymer network has a high softening temperature of 319° C., as measured by DSC.

Multifunctional phthalonitrile monomer resins are a class of network forming resins that, when polymerized, supply excellent thermal stability and degradation resistance. Phthalonitriles undergo an addition polymerization reaction when promoted by a catalyst or curative. Known catalyst systems for phthalonitrile polymerization are the addition of a base and an alcohol and heat, the addition of a suitable reducing agent and heat, and the addition of metals or organometals or metal salts and heat (U.S. Pat. No. 4,304,896 to Keller et al.). Many metals have been shown to result in phthalonitrile polymerization (McKeown, N. B., *The Synthesis of Symmetrical Phthalocyanines, in The Porphyrin Handbook*, K. M. Kadish, K. M. Smith, and R. Guilard, Editors. 2003, Academic Press: Amsterdam. p. 61-124). Aromatic amines, alcohols and thiols act as phthalonitrile curatives (U.S. Pat. No. 4,408,035 to Keller and U.S. Pat. No. 4,223,123 to Keller et al.). The catalyst or curative promoted phthalonitrile polymerization reaction proceeds at an appreciable rate between temperatures of 200 to 250 degrees Celsius. Phthalonitrile polymerized networks have demonstrated excellent thermal stability imparted by a high glass transition temperature, good thermal and thermooxidative degradation resistance, inherent non-flammability and low moisture uptake (Dominguez, D. D. and T. M. Keller, *Properties of phthalonitrile monomer blends and thermosetting phthalonitrile copolymers*. Polymer, 2007, 48(1): p. 91-97).

Example suitable phthalonitrile resins as the one or more phthalonitrile resin(s) in resin blends according to the present disclosure include for instance and without limitation, bis(3,4-dicyanophenyl) ether of bisphenol A, bis(2,3-dicyanophenyl) ether of bisphenol A, bis(3,4-dicyanophenyl) ether of bisphenol AP, bis(3,4-dicyanophenyl) ether of bisphenol AF, bis(3,4-dicyanophenyl) ether of bisphenol B, bis(3,4-dicyanophenyl) ether of bisphenol BP, bis(3,4-dicyanophenyl) ether of bisphenol C, bis(3,4-dicyanophenyl) ether of bisphenol C2, bis(3,4-dicyanophenyl) ether of bisphenol E, bis(3,4-dicyanophenyl) ether of bisphenol F, bis(3,4-dicyanophenyl) ether of 3,3',5,5'-tetramethylbisphenol F, bis(3,4-dicyanophenyl) ether of bisphenol FL, bis(3,4-dicyanophenyl) ether of bisphenol G, bis(3,4-dicyanophenyl) ether of bisphenol M, bis(3,4-dicyanophenyl) ether of bisphenol S, bis(3,4-dicyanophenyl) ether of bisphenol P, bis(3,4-dicyanophenyl) ether of bisphenol PH, bis(3,4-dicyanophenyl) ether of bisphenol T, bis(3,4-dicyanophenyl) ether of bisphenol TMC, bis(3,4-dicyanophenyl) ether of bisphenol Z, bis(3,4-dicyanophenyl) ether of 4,4'-dihydroxybiphenyl, bis(3,4-dicyanophenyl) ether of 4,4'-dihydroxydiphenyl ether, bis(3,4-dicyanophenyl) ether of catechol, bis(3,4-dicyanophenyl) ether of 4,4'-dihydroxybenzophenone, 3,4-dicyanophenyl ether of phenol, 2,3-dicyanophenyl ether of phenol, 4-tert-butylphthalonitrile, 4-butoxyphthalonitrile, 3,4-dicyanophenyl ether of 4-cumylphenol, 3,4-dicyanophenyl ether of 2-allylphenol, 3,4-dicyanophenyl ether of eugenol, bis(3,4-dicyanophenyl) ether of resorcinol. In certain embodiments, a suitable phthalonitrile resin is independently selected from bis(3,4-dicyanophenyl) ether of resorcinol, bis(3,4-dicyanophenyl) ether of bisphenol A, bis(3,4-dicyanophenyl) ether of bisphenol M, bis(3,4-dicyanophenyl) ether of bisphenol P, bis(3,4-dicyanophenyl) ether of bisphenol T, or a combination thereof. In select embodiments, the phthalonitrile resin is bis(3,4-dicyanophenyl) ether of bisphenol M. In select embodiments, the phthalonitrile resin is bis(3,4-dicyanophenyl) ether of bisphenol T. Typically, the resin blend (including one or more resins) is a solid at 25° C.

Bis(3,4-dicyanophenyl) ether of bisphenol M is also referred to as "bisphenol M diphthalonitrile ether resin" or "BMPN". In resin blends of the present disclosure, usually BMPN is of Formula IV:

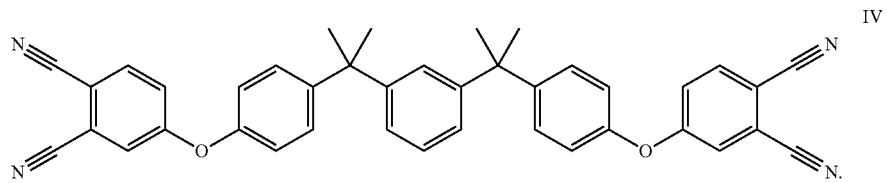 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

Bis(3,4-dicyanophenyl) ether of bisphenol T is also referred to as "bisphenol T diphthalonitrile ether resin" or "BTPN". In resin blends of the present disclosure, usually BTPN is of Formula V:

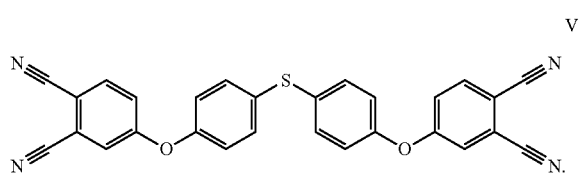 [SMILES: N#Cc1ccc(Oc2ccc(Sc3ccc(Oc4ccc(C#N)c(C#N)c4)cc3)cc2)cc1C#N]

In certain embodiments, the phthalonitrile resin comprises a bisphenol M diphthalonitrile ether resin of Formula IV. In certain embodiments, the phthalonitrile resin comprises a bisphenol P diphthalonitrile ether resin. In some embodiments, the first phthalonitrile resin comprises a bisphenol T diphthalonitrile ether resin of Formula V. In certain embodiments, the first phthalonitrile resin comprises a resorcinol diphthalonitrile ether resin.

When two phthalonitrile resins are included in the resin blend, the amounts of the two phthalonitrile resins is not particularly limited. In some embodiments, a weight ratio of a first phthalonitrile resin to a second phthalonitrile resin ranges from 10:90 to 90:10, inclusive; or from 15:85 to 85:15, inclusive; or from 30:70 to 70:30, inclusive. In certain embodiments, the resin blend comprises a blend of each of the monomers of Formula IV, Formula V, bisphenol P diphthalonitrile ether resin (BPPN), and resorcinol diphthalonitrile ether resin (RPN).

Synthesis of BMPN, BPPN, RPN, and BTPN can be achieved by the nucleophilic substitution of the nitro group of 4-nitrophthalonitrile by phenolic residues of the bisphenols catalyzed by potassium carbonate in DMSO. The reactions can be conducted at ambient temperature under a nitrogen atmosphere.

Advantageously, 4-S-(5-amino-1,3,4-thiadiazole-2-mercapto)phthalonitrile has been discovered to be useful as a curative of phthalonitrile resins. The 4-(5-amino-1,3,4-thiadiazole-2-mercapto)phthalonitrile can be added to a multifunctional phthalonitrile resin as demonstrated herein by each of bisphenol M diphthalonitrile and bisphenol T diphthalonitrile. For instance, the 4-S-(5-amino-1,3,4-thiadiazole-2-mercapto)phthalonitrile can be dissolved into a bisphenol based phthalonitrile resin at a temperature above the melt temperature of the bisphenol phthalonitrile resin, i.e. 165° C. for bisphenol M diphthalonitrile and 185° C. for bisphenol T diphthalonitrile. Continued heating of the resin system after addition of 4-S-(5-amino-1,3,4-thiadiazole-2-mercapto)phthalonitrile leads to gelation of the phthalonitrile to a solid. The phthalonitrile polymerized network offers a stiff polymer network with a high softening temperature, thermal and oxidative degradation resistance, low water absorption, inflammability, and good adhesion to many surfaces.

A method of making a polymerized network typically includes combining a phthalonitrile resin and a curative (e.g., 4-S-(5-amino-1,3,4-thiadiazole-2-mercapto)phthalonitrile), and optionally a catalyst, to form a resin blend (or monomer blend); and subjecting the resin blend to heat, often heat at a temperature of no more than 300° C., to form a fully polymerized network. Generally, the composition is heated to a temperature between about 50° C. and 300° C., such as between about 130-300° C., for a time of about 1-480 minutes. Suitable sources of heat include induction heating coils, ovens, hot plates, heat guns, infrared sources including lasers, microwave sources.

Suitable optional catalysts include for instance and without limitation, a base such as 1,5-diazabicyclo(4.3.0)non-5-ene or 1,8-diazabicyclo[5.4.0]undec-7-ene; reducing agents such as hydroquinone and 1,2,3,6-tetrahydropyridine; metal, organometals or metal salts such as copper, iron, copper acetylacetonate, zinc naphthenate, dibutyltin dilaurate, stannous chloride, stannic chloride, copper chloride, iron chloride, and/or calcium carbonate.

Solvents can be used as a processing aid. Useful solvents are ketones such as acetone, methyl ethyl ketone, methyl isobutyl ketone, cyclopentanone and cyclohexanone; amides such as acetamide, formamide, N,N-dimethylforamide, N-methylpyrrolidinone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl)ethanol, 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, methyl cellosolve acetate, methyl formate; and other solvents such as tetrahydrofuran, methylene chloride, dichloromethane, chloroform, acetonitrile, nitromethane, glycol sulfite and 1,2-dimethoxyethane (glyme).

In some embodiments, the resin blend is subjected to a temperature of no more than 300 degrees Celsius (° C.) in air. Optionally, the resin blend is subjected to a temperature of no more than 300 degrees Celsius at ambient pressure.

Compositions according to at least certain embodiments of the disclosure include one or more curatives. Such curatives often include an amine compound, such as a primary amine, for instance including an aniline functional residue. Combinations of various curatives can be used if desired. The curative is typically present in an amount of at least 1 wt. % or more of the resin blend, 2 wt. %, 5 wt. %, 10 wt. %, 15 wt. %, or even 20 wt. % or more of the resin blend; and up to 40 wt. % of the resin blend, 35 wt. %, 30 wt. %, or even up to 25 wt. % of the resin blend; such as between 0 and 40 wt. % of the resin blend. Higher molecular weight and lower volatility aniline functional curatives are typically desired to avoid loss of the curative during polymerization. Dianiline based curatives can be of value due to a higher aniline functionality per weight of the curative. Example dianiline based curatives that will promote phthalonitrile polymerization include for instance and without limitation, 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy) dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, and 4,4'-diaminobenzophenone. The primary amine promoted phthalonitrile cure reaction proceeds at an appreciable rate between temperatures of 200° C. to 250° C. Amine cured phthalonitrile polymerized networks have demonstrated excellent thermal stability imparted by a high glass transition temperature, good thermal and thermoxidative degradation resistance, plus are inherently non-flammable, and have low moisture uptake.

Certain other optional additives may also be included in resin blends according to the present disclosure, including, for example, tougheners, fillers, and combinations thereof. Such additives provide various functions. For instance, a toughening agent such as organic particles, may add strength to the composition after curing without interfering with curing. It will be understood by one of skill in the art that one compound may form two or more different functions. For example, a compound may function as both a toughening agent and a filler. In some embodiments, such additives will not react with the resins of the resin blend. In some embodiments, such additives may include reactive functional groups, particularly as end groups. Examples of such reactive functional groups include, but are not limited to, amines, thiols, alcohols, epoxides, vinyls, and combinations thereof.

Useful toughening agents are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski). Exemplary rubbery backbones include polymerized butadiene or a polymerized mixture of butadiene and styrene. Exemplary shells including polymerized methacrylic acid esters are lower alkyl (C1-C4) substituted methacrylates. Exemplary monovinyl aromatic hydrocarbons are styrene, alpha-methylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would interfere with the polymerization of the resin.

Examples of useful toughening agents of the second type are acrylate core-shell graft copolymers wherein the core or backbone is a polyacrylate polymer having a glass transition temperature below 0° C., such as polybutyl acrylate or polyisooctyl acrylate to which is grafted a polymethacrylate polymer (shell) having a glass transition above 25° C., such as polymethylmethacrylate.

The third class of useful toughening agents includes elastomeric particles that have a glass transition temperature ($T_g$) below 25° C. before mixing with the other components of the composition. These elastomeric particles are polymerized from free radical polymerizable monomers and a copolymerizable polymeric stabilizer. The free radical polymerizable monomers are ethylenically unsaturated monomers or diisocyanates combined with co-reactive difunctional hydrogen compounds such as diols, diamines, and alkanolamines.

Useful toughening agents include core/shell polymers, such as methacrylate-butadiene-styrene (MBS) copolymer wherein the core is crosslinked styrene/butadiene rubber and the shell is polymethylacrylate (for example, those available under the trade names ACRYLOID KM653 and KM680, from Rohm and Haas, Philadelphia, PA), those having a core including polybutadiene and a shell including poly(methyl methacrylate) (for example, those available under the trade names KANE ACE M511, M521, B11A, B22, B31, and M901 from Kaneka Corporation, Houston, TX and CLEARSTRENGTH C223 from ATOFINA, Philadelphia, PA), those having a polysiloxane core and a polyacrylate shell (for example, those available under the trade names CLEARSTRENGTH S-2001 from ATOFINA and GENIOPERL P22 from Wacker-Chemie GmbH, Wacker Silicones, Munich, Germany), those having a polyacrylate core and a poly(methyl methacrylate) shell (for example, those available under the trade names PARALOID EXL2330 from Rohm and Haas and STAPHYLOID AC3355 and AC3395 from Takeda Chemical Company, Osaka, Japan), those having an MBS core and a poly(methyl methacrylate) shell (for example, those available under the trade names PARALOID EXL2691A, EXL2691, and EXL2655 from Rohm and Haas); and the like; and mixtures thereof.

As used above, for acrylic core/shell materials "core" will be understood to be an acrylic polymer having a $T_g$ of less than 0° C. and "shell" will be understood to be an acrylic polymer having a $T_g$ of greater than 25° C.

Other useful toughening agents include: carboxylated and amine terminated acrylonitrile/butadiene vulcanizable elastomer precursors, such as those available under the trade names HYCAR CTBN 1300X8, ATBN 1300X16, and HYCAR 1072 from B. F. Goodrich Chemical Co.; butadiene polymers, such as those available under the trade name HYCAR CTB; amine functional polyethers such as HC1 101 (i.e., polytetramethylene oxide diamine) a 10,000 MW, primary amine-terminated, compound from 3M Co., St. Paul, MN, and those available under the trade name JEFFAMINE from Huntsman Chemical Co., Houston, TX Useful liquid poly-butadiene hydroxyl terminated resins include those available under the trade names LIQUIFLEX H by Petroflex of Wilmington, DE, and HT 45 by Sartomer of Exton, PN.

Tougheners may include epoxy-terminated compounds, which can be incorporated into the polymer backbone. A typical, preferred, list of tougheners includes: acrylic core/shell polymers; styrene-butadiene/methacrylate core/shell polymers; polyether polymers; carboxylated acrylonitrile/butadienes; and carboxylated butadienes. Advantages can be obtained from the provision of the chain extension agent in a composition with an epoxy resin even in the absence of a toughening agent as described above. However, particular advantage is achieved from the presence of the toughening agent or combinations of different agents, as previously suggested.

Various combinations of toughening agents can be used if desired. If used, a toughening agent is present in the resin blend in an amount of at least 3 wt. % or at least 5 wt. %. If used, a toughening agent is present in a resin blend in an amount of no greater than 35 wt. % or no greater than 25 wt. %.

A filler to optionally be included in the resin blends according to the present disclosure is not particularly limited, and may include nanoparticles, microparticles, discontinuous fibers, continuous fibers, and combinations thereof. The term "particles" encompasses nanoparticles, microparticles, and combinations thereof. For instance, particles of a metal carbide include both metal carbide nanoparticles and metal carbide microparticles. In certain embodiments, the filler comprises a nanofiller comprising metal carbide nanoparticles, metal oxide nanoparticles, silica nanoparticles, carbon nanoparticles, metal carbonate nanoparticles, metal nitride nanoparticles, metal hydroxide nanoparticles, metal sulfate nanoparticles, barium titanate nanoparticles, or a combination thereof. Optionally, the filler comprises a nanofiller comprising calcite nanoparticles, silica nanoparticles, silicon carbide nanoparticles, alumina nanoparticles, zirconia nanoparticles, magnesium oxide nanoparticles, aluminum nitride nanoparticles, boron nitride nanoparticles, dolomite nanoparticles, boehmite nanoparticles, magnesium hydroxide nanoparticles, calcium sulfate nanoparticles, barium sulfate nanoparticles, magnesium sulfate nanoparticles, or a combination thereof. As used herein, the term "nano" or "micro" in front of a material is interchangeable with reference of that material as a nanoparticle or microparticle, respectively (e.g., "nanosilica" is interchangeable with "silica nanoparticles", "microcalcite" is interchangeable with "calcite microparticles", etc.). For instance and without limitation, some suitable nanoparticles include silica nanoparticles available from Nalco Company (Naperville, IL) under the trade designation NALCO 15827; and silicon carbide nanoparticles available from 3M Technical Ceramics (Kempten, Germany) under the trade designation VSN1393.

Typically, a nanofiller can be present in resin blends according to the present disclosure in an amount of 1 wt. % or more, based on the total weight of the resin blend, 3 wt. %, 5 wt. %, 8 wt. %, 10 wt. %, 12 wt. %, 15 wt. %, 20 wt. %, or even 25 wt. % or more, based on the total weight of the resin blend; and 40 wt. % or less, 38 wt. % or less, 36 wt. %, 34 wt. %, 32 wt. %, 30 wt. %, 28 wt. %, 26 wt. %, 24 wt. %, 22 wt. %, 20 wt. %, 18 wt. %, or 15 wt. % or less, based on the total weight of the resin blend. Stated another way, a nanofiller may be present in a resin blend in an amount of 1 to 40 wt. %, 1 to 20 wt. %, 3 to 15 wt. %, 20 to 40 wt. %, or 25 to 40 wt. %, based on the total weight of the resin blend.

In certain embodiments, the optional filler comprises a microfiller comprising metal carbide microparticles, metal oxide microparticles, silica microparticles, carbon microparticles, metal carbonate microparticles, metal nitride microparticles, metal hydroxide nanoparticles, metal sulfate microparticles, barium titanate microparticles, cenospheres, or a combination thereof. Optionally, the filler comprises a microfiller comprising calcite microparticles, silica microparticles, silicon carbide microparticles, alumina microparticles, magnesium oxide microparticles, aluminum nitride microparticles, boron nitride microparticles, dolomite microparticles, boehmite microparticles, glass bubbles, or a combination thereof. For instance and without limitation, some suitable microparticles include boron nitrile microparticles available from 3M Company (St. Paul, MN) under the trade designation 3M BORON NITRIDE COOLING FILLER PLATELETS; glass bubbles available from 3M Company (St. Paul, MN) under the trade designation 3M GLASS BUBBLES IM16K; and alumina microparticles available from Micron Corp (a subsidiary of the Nippon Steel and Sumikin Materials Co., Japan) under the trade designation MICRON TA6Y1 ALUMNA.

Typically, a microfiller can be present in resin blends according to the present disclosure in an amount of 1 wt. % or more, based on the total weight of the resin blend, 5 wt. %, 10 wt. %, 15 wt. %, 20 wt. %, 30 wt. %, 40 wt. %, 50 wt. %, or even 60 wt. % or more, based on the total weight of the resin blend; and 90 wt. % or less, 85 wt. %, 80 wt. %, 75 wt. %, 70 wt. %, 65 wt. %, 55 wt. %, 45 wt. %, 35 wt. %, or 25 wt. % or less, based on the total weight of the resin blend. Stated another way, a nanofiller may be present in a resin blend in an amount of 1 to 90 wt. %, 1 to 50 wt. %, 5 to 35 wt. %, 20 to 55 wt. %, or 60 to 90 wt. %, based on the total weight of the resin blend.

In certain embodiments, the filler comprises particles of a metal carbide, a metal oxide, silica, carbon, a metal carbonate, a metal nitride, a metal hydroxide, a metal sulfate, barium titanate, glass bubbles, cenospheres, or a combination thereof. In certain embodiments, the filler comprises particles of calcite, silica, silicon carbide, alumina, zirconia, magnesium oxide, aluminum nitride, boron nitride, dolomite, boehmite, magnesium hydroxide, calcium sulfate, barium sulfate, magnesium sulfate, or a combination thereof.

Generally, the optional surface modifiers of the present disclosure include at least a binding group and a compatibilizing segment. The compatibilizing segment is selected to improve the compatibility of filler with the curable resin. Generally, the selection of the compatibilizing group depends on a number of factors including the nature of the curable resin, the concentration of the filler, and the desired degree of compatibility. Useful compatibilizing groups include for instance and without limitation, polyalkylene oxide residues (e.g., polypropylene oxide, polyethylene oxide, and combinations thereof), aromatic residues (e.g. phenyl, phenylalkylene, substituted phenylene, and combinations thereof, carbonyl residues (e.g., ketone, ester, amide, carbamate, and combinations thereof). The binding group bonds to the particle surface, connecting the surface-modifying agent to the filler. In the case of calcite particles, unlike many silica-based nanoparticle systems wherein the surface-modifying agents are covalently bonded to the silica, the surface-modifying agents of the present disclosure are ionically bonded to or physically bonded to (e.g., associated with) the calcite particles. Depending on the filler surface and the surface modifier, the surface modifier may be one or more of covalently bonded, ionically bonded, or physically bonded to a surface of the filler.

Some suitable surface modifiers comprise an organoacid, an organobase, a siloxane, a silane, or a combination thereof. The type of surface modifier will depend on the material of the filler. For instance, the surface modifier may comprise a silane or a siloxane when the filler comprises silica nanoparticles, silica microparticles, cenospheres, zirconia nanoparticles, zirconia microparticles, magnesium oxide nanoparticles, magnesium oxide microparticles, silicon carbide nanoparticles, silicon carbide microparticles, or a combination thereof. The surface modifier may comprise an organoacid or an organobase when the filler comprises calcite nanoparticles, calcite microparticles, magnesium oxide nanoparticles, magnesium oxide microparticles, alumina nanoparticles, alumina microparticles, dolomite nanoparticles, dolomite microparticles, boehmite nanoparticles, boehmite microparticles, or a combination thereof. The surface modifier may comprise an organoacid when the filler comprises zirconia nanoparticles, zirconia microparticles, magnesium oxide nanoparticles, magnesium oxide microparticles, or a combination thereof. The surface modifier may comprise an organosulfonate and/or an organophosphate when the filler comprises calcite nanoparticles, calcite microparticles, or a combination thereof. For example, the sulfonate and phosphate ends of organosulfonates and organophosphates, respectively, associate with the calcite surface by the formation of an ionic complex between sulfonate and phosphate of the surface modifier and calcium of the calcite. The organic end of the surface modifier stabilizes the calcite in the phthalonitrile resin, resulting in a calcite dispersion in the liquid resin melt and stabilized calcite in the cured polymer network. At least certain embodiments of the present disclosure utilize polypropylene oxide and polyethylene oxide as the organic end of any of the surface modifiers described herein, associated with the monomer resin and polymer network.

For instance, surface modification of certain particles is described in PCT Application Publication No. WO 2017/173195 (Anderson et al.).

At temperatures near to 60 degrees Celsius, solvent is often added to reduce the viscosity of the resin. Some suitable solvents miscible with phthalonitrile resins include methyl ethyl ketone (MEK), methyl isobutyl ketone (MIBK), diacetone alcohol, dimethylformamide (DMF), and dimethyl sulfoxide (DMSO). At higher temperatures (e.g., greater than 120° C. but less than 200° C.), mixing and milling can be performed without the addition of solvent in a liquid resin melt. An advantage of high temperature mixing and milling is the removal of solvent stripping.

A surface modifying agent for a filler surface is selected such that one end of the surface modifier preferentially associates with the filler surface and the other end of the surface modifier preferentially associates with the monomer resin and maintains particle compatibility in the resin and polymerized network. The concentration of a surface modifier can be tuned to minimize free surface modifier in the resin and avoid open filler (e.g., calcite) surface, both of which would catalyze phthalonitrile polymerization over 200° C.

In certain embodiments, the optional filler comprises at least one of reinforcing continuous fibers or reinforcing discontinuous fibers, for instance as described in PCT Application Publication No. WO 2017/173195 (Anderson et al.).

The amount of optional discontinuous fibers dispersed in the resin blend is not particularly limited. The plurality of fibers is often present in an amount of 1 wt. % or more of the resin blend, 2 wt. %, 3 wt. %, 5 wt. %, 10 wt. %, 15 wt. %, 20 wt. %, or 25 wt. % or more of the resin blend; and up to 50 wt. %, 45 wt. %, 40 wt. %, or up to 35 wt. % of the resin blend. In certain embodiments, the fibers are present in the resin blend in an amount of 1 to 50 wt. %, 2 to 25 wt. %, or 5 to 15 wt. %, inclusive, of the resin blend. In certain embodiments, discontinuous fibers are present in an amount of 5 to 50 wt. %, inclusive, of the resin blend.

Other optional additives, or adjuvants, may be added to the compositions as desired. Examples of such other optional additives include as colorants, anti-oxidant stabilizers, thermal degradation stabilizers, light stabilizers, flow agents, bodying agents, flatting agents, additional fillers, binders, blowing agents, fungicides, bactericides, surfactants, plasticizers, rubber tougheners, and other additives known to those skilled in the art. Such additives are typically substantially unreactive. These adjuvants, if present, or other optional additives, are added in an amount effective for their intended purpose.

Examples of additional suitable filler materials include reinforcement-grade carbon black, fluoroplastics, clays, and any combination of any of these in any proportions.

The phrase "reinforcement-grade carbon black" as used herein, includes any carbon black with an average particle size smaller than about 10 microns. Some particularly suitable average particle sizes for reinforcement-grade carbon black range from about 9 nm to about 40 nm. Carbon black that is not reinforcement grade include carbon black with an average particle size larger than about 40 nm. Carbon nanotubes are also useful fillers. Carbon black fillers are typically employed as a means to balance, elongation, hardness, abrasion resistance, conductivity, and processibility of compositions. Suitable examples include MT blacks (medium thermal black) designated N-991, N-990, N-908, and N-907; FEF N-550; and large particle size furnace blacks. Further useful fillers include diatomaceous earth, barium sulfate, talc, and calcium fluoride. The choice and amounts of optional components depend on the needs of the specific application.

Various embodiments are provided that include resin blends, articles, compounds, and methods.

Embodiment 1 is a resin blend. The resin blend includes a blend of at least one phthalonitrile resin and a compound of Formula I:

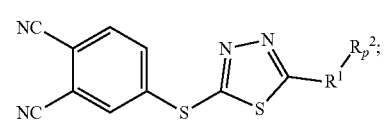

wherein p is 0 or 1. When p is 0, $R^1$ is H, an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH(=O), —C(=O)—N—$R_2^4$, —S($O_2$)—$R^5$, a carboxylic acid group, or a halogen, wherein $R^3$ is an alkyl group, each $R^4$ is independently H or an alkyl group, and $R^5$ is H or an alkyl group. When p is 1, $R^1$ is a covalent bond, an arylene group, or an aralkylene group, and $R^2$ is an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH (=O), —C(=O)—N—R₂⁴, —S(O₂)—R⁵, a carboxylic acid group, or a halogen, wherein R³ is an alkyl group, each R⁴ is independently H or an alkyl group, and R⁵ is H or an alkyl group.

Embodiment 2 is the resin blend of embodiment 1, wherein p is 0 and R¹ is H, an alkyl group, a heteroalkyl group, or an amino group.

Embodiment 3 is the resin blend of embodiment 1 or embodiment 2, wherein p is 0 and R¹ is an amino group.

Embodiment 4 is the resin blend of embodiment 1 or embodiment 2, wherein p is 0 and R¹ is methyl.

Embodiment 5 is the resin blend of embodiment 1 or embodiment 2, wherein p is 0 and R¹ is —S—CH₃.

Embodiment 6 is the resin blend of embodiment 1 or embodiment 2, wherein p is 0 and R¹ is H.

Embodiment 7 is the resin blend of any of embodiments 1 to 6, wherein the at least one phthalonitrile resin is independently selected from bis(3,4-dicyanophenyl) ether of bisphenol A, bis(2,3-dicyanophenyl) ether of bisphenol A, bis(3,4-dicyanophenyl) ether of bisphenol AP, bis(3,4-dicyanophenyl) ether of bisphenol AF, bis(3,4-dicyanophenyl) ether of bisphenol B, bis(3,4-dicyanophenyl) ether of bisphenol BP, bis(3,4-dicyanophenyl) ether of bisphenol C, bis(3,4-dicyanophenyl) ether of bisphenol C2, bis(3,4-dicyanophenyl) ether of bisphenol E, bis(3,4-dicyanophenyl) ether of bisphenol F, bis(3,4-dicyanophenyl) ether of 3,3',5,5'-tetramethylbisphenol F, bis(3,4-dicyanophenyl) ether of bisphenol FL, bis(3,4-dicyanophenyl) ether of bisphenol G, bis(3,4-dicyanophenyl) ether of bisphenol M, bis(3,4-dicyanophenyl) ether of bisphenol S, bis(3,4-dicyanophenyl) ether of bisphenol P, bis(3,4-dicyanophenyl) ether of bisphenol PH, bis(3,4-dicyanophenyl) ether of bisphenol T, bis(3,4-dicyanophenyl) ether of bisphenol TMC, bis(3,4-dicyanophenyl) ether of bisphenol Z, bis(3,4-dicyanophenyl) ether of 4,4'-dihydroxybiphenyl, bis(3,4-dicyanophenyl) ether of 4,4'-dihydroxydiphenyl ether, bis(3,4-dicyanophenyl) ether of catechol, bis(3,4-dicyanophenyl) ether of 4,4'-dihydroxybenzophenone, 3,4-dicyanophenyl ether of phenol, 2,3-dicyanophenyl ether of phenol, 4-tert-butylphthalonitrile, 4-butoxyphthalonitrile, 3,4-dicyanophenyl ether of 4-cumylphenol, 3,4-dicyanophenyl ether of 2-allylphenol, 3,4-dicyanophenyl ether of eugenol, bis(3,4-dicyanophenyl) ether of resorcinol, or a combination thereof.

Embodiment 8 is the resin blend of any of embodiments 1 to 7, wherein the at least one phthalonitrile resin is independently selected from bis(3,4-dicyanophenyl) ether of resorcinol, bis(3,4-dicyanophenyl) ether of bisphenol A, bis(3,4-dicyanophenyl) ether of bisphenol M, bis(3,4-dicyanophenyl) ether of bisphenol P, bis(3,4-dicyanophenyl) ether of bisphenol T, or a combination thereof.

Embodiment 9 is the resin blend of any of embodiments 1 to 8, wherein the compound of Formula I is present in an amount of 1 to 70 weight percent (wt. %), based on the total weight of the at least one phthalonitrile resin.

Embodiment 10 is the resin blend of any of embodiments 1 to 9, wherein the compound of Formula I is present in an amount of 1 to 20 wt. %, based on the total weight of the at least one phthalonitrile resin.

Embodiment 11 is the resin blend of any of embodiments 1 to 10, further including at least one additive.

Embodiment 12 is the resin blend of embodiment 11, wherein the at least one additive is independently selected from a toughener, a filler, or a combination thereof.

Embodiment 13 is the resin blend of embodiment 12, wherein the filler includes particles of a metal carbide, a metal oxide, silica, carbon, a metal carbonate, a metal nitride, a metal hydroxide, a metal sulfate, barium titanate, glass bubbles, cenospheres, or a combination thereof.

Embodiment 14 is the resin blend of embodiment 11 or embodiment 12, wherein the filler includes particles of calcite, silica, silicon carbide, alumina, zirconia, magnesium oxide, aluminum nitride, boron nitride, dolomite, boehmite, magnesium hydroxide, calcium sulfate, barium sulfate, magnesium sulfate, or a combination thereof.

Embodiment 15 is an article including a polymerization product of the resin blend of any of embodiments 1 to 14.

Embodiment 16 is a compound of Formula II:

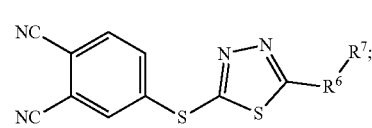

wherein R⁶ is a covalent bond, an arylene group, or an aralkylene group, and R⁷ is a hydroxyl group, a thiol group, —S—R⁸, wherein R⁸ is an alkyl group, or an amino group.

Embodiment 17 is the compound of embodiment 16, wherein R⁶ is a covalent bond.

Embodiment 18 is the compound of embodiment 16, wherein R⁶ is an arylene group that is a phenylene group.

Embodiment 19 is the compound of embodiment 16, wherein R⁶ is an aralkylene group comprising a phenylene group.

Embodiment 20 is the compound of any of embodiments 16 to 19, wherein R⁷ is an amino group.

Embodiment 21 is the compound of any of embodiments 16 to 19, wherein R⁷ is a hydroxyl group.

Embodiment 22 is the compound of any of embodiments 16 to 19, wherein R⁷ is —S—CH₃.

Embodiment 23 is an article including a polymerized reaction product of the compound of Formula II of any of embodiments 16 to 22.

Embodiment 24 is a method of making a compound of Formula II:

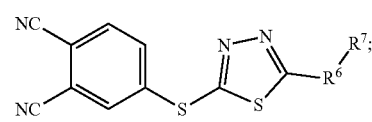

wherein R⁶ is a covalent bond, an arylene group, or an aralkylene group, and R⁷ is a hydroxyl group, a thiol group, —S—R⁸, wherein R⁸ is an alkyl group, or an amino group. The method includes a) combining components to form a mixture, and b) reacting the mixture with stirring. The components include:
i) 4-nitrophthalonitrile;
ii) a compound of Formula III:

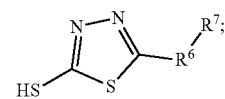

wherein R⁶ and R⁷ are as defined for Formula II;
iii) an aprotic solvent; and
iv) a base.

Embodiment 25 is the method of embodiment 24, further including heating the mixture.

Embodiment 26 is the method of embodiment 24 or embodiment 25, further including cooling the mixture.

Embodiment 27 is the method of any of embodiments 24 to 26, wherein the aprotic solvent is selected from the group consisting of dimethylsulfoxide (DMSO), dimethyl formamide (DMF), dimethylacetamide (DMAc), N-methylpyrrolidone (NMP), hexamethylphosphoramide (HMPA), tetrahydrofuran (THF), or a combination thereof.

Embodiment 28 is the method of any of embodiments 24 to 27, wherein the base is selected from the group consisting of triethylamine, tributylamine, potassium carbonate, sodium carbonate, potassium hydroxide, sodium hydroxide, 1,4-diazabicyclo[2.2.2]octane (DABCO), pyridine, or a combination thereof.

Embodiment 29 is the method of any of embodiments 24 to 28, wherein $R^6$ is a covalent bond.

Embodiment 30 is the method of any of embodiments 24 to 28, wherein $R^6$ is an arylene group that is a phenylene group.

Embodiment 31 is the method of any of embodiments 24 to 28, wherein $R^6$ is an aralkylene group including a phenylene group.

Embodiment 32 is the method of any of embodiments 24 to 31, wherein $R^7$ is an amino group.

Embodiment 33 is the method of any of embodiments 24 to 31, wherein $R^7$ is a hydroxyl group.

Embodiment 34 is the method of any of embodiments 24 to 31, wherein $R^7$ is —S—$CH_3$.

Embodiment 35 is the method of any of embodiments 24 to 34, further including adding molecular sieves to the reaction mixture.

Embodiment 36 is the method of any of embodiments 24 to 35, wherein the mixture is reacted for 2 to 20 hours.

Embodiment 37 is the method of any of embodiments 24 to 36, further including precipitating the compound of Formula II from the reaction mixture in a blend of water and alcohol.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated. All materials are commercially available, for example from Sigma-Aldrich Chemical Company; Milwaukee, WI, or known to those skilled in the art unless otherwise stated or apparent.

These abbreviations are used in the following examples: g=gram, hr=hour, kg=kilograms, min=minutes, mol=mole; cm=centimeter, mm=millimeter, nm=nanometer, mL=milliliter, L=liter, MPa=megaPascals, %=percent, and wt.=weight.

TABLE 1

| Material | Details | Source |
| --- | --- | --- |
| DMSO | Dimethyl sulfoxide, $(CH_3)_2SO$ | Sigma Aldrich Chemical Company, St. Louis, MO |
| 2-mercapto-1,3,4-thiadiazole | $C_2H_2N_2S_2$ | Sigma Aldrich Chemical Company |
| 5-amino-2-mercapto-1,3,4-thiadiazole | $C_2H_3N_3S_2$ | Sigma Aldrich Chemical Company |
| 5-methyl-2-mercapto-1,3,4-thiadiazole | $C_3H_4N_2S_2$ | Sigma Aldrich Chemical Company |
| 5-methylmercapto-2-mercapto-1,3,4-thiadiazole | $C_3H_4N_2S_3$ | Sigma Aldrich Chemical Company |
| Potassium carbonate | $K_2CO_3$ | Sigma Aldrich Chemical Company |
| Triethylamine | $(C_2H_5)_3N$ | Sigma Aldrich Chemical Company |
| 4-nitrophthalonitrile | $O_2NC_6H_3$-1,2-$(CN)_2$ | Sigma Aldrich Chemical Company |
| Molecular sieves | 3 Å molecular sieves, 1-2 mm pellets | Sigma Aldrich Chemical Company |
| 4,4'-(1,3-phenylenedioxy)dianiline | $C_6H_4(OC_6H_4NH_2)_2$ | Sigma Aldrich Chemical Company |
| BMPN | Bisphenol M diphthalonitrile (i.e., bis(3,4-dicyanophenyl) ether of bisphenol M) | Prepared as described in Preparatory Example A of PCT Application Publication No. WO2017/173040 |
| BTPM | Bisphenol T diphthalonitrile (i.e., bis(3,4-dicyanophenyl) ether of bisphenol T) | Prepared as described in Preparatory Example C of PCT Application Publication No. WO2017/173040 |

Method of Measuring Cure Reaction Exotherm Via Differential Scanning Calorimeter (DSC)

A TA Instruments Q Series DSC (obtained from TA Instruments, New Castle, DE) was used to measure the dynamic heat flow of a material under application of a constant thermal ramp rate. Approximately 5 mg of resin was weighed into an aluminum DSC pan. The sample pan was loaded into the DSC instrument, and the heat flow of the sample was measured in a dynamic DSC measurement with a thermal ramp rate of 1 degree Celsius per minute (° C./min).

Method of Measuring Melting Point Temperature Via DSC

A TA Instruments Q Series DSC (obtained from TA Instruments, New Castle, DE) was used to measure the dynamic heat flow of a material under application of a constant thermal ramp rate. Approximately 5 mg of resin was weighed into an aluminum DSC pan. The sample pan was loaded into the DSC instrument, and the heat flow of the sample was measured in a dynamic DSC measurement with a thermal ramp rate of 10 degree Celsius per minute (° C./min). The melting point temperature was measured as the peak temperature of the endothermic melting transition peak.

Method of Measuring the Dynamic Mechanical Properties Via a Dynamic Mechanical Analyzer (DMA)

A TA Instruments Q Series DMA (obtained from TA Instruments, New Castle, DE) was used to measure low strain linear viscoelastic properties. Dynamic mechanical measurements were performed using single cantilever beam geometry. The low strain in-phase and out-of-phase deformation response was measured when applying a continuous oscillatory force with a controlled deformation amplitude of 20 micrometers at a frequency of 1 Hz, and the resulting storage and loss moduli and loss tangent were calculated ramping the temperature during the measurement. The temperature was ramped at 3° C./min.

Method of Measuring Fourier Transform Infrared (FTIR) Absorbance Spectroscopy

A Thermo Scientific Nicolet 6700 FTIR spectrometer with Smart iTR accessory (obtained from Thermo Fisher Scientific, Waltham, MA) was used to measure infrared absorbance by attenuated total reflectance (ATR). The spectral absorbance features that define the carbon-nitrogen triple bond stretch of the nitrile and the carbon-carbon double bond stretch of the allyl were measured for the phthalonitrile monomer system (resin+diluent) and the polymerized polymer network.

Method of Measuring Nuclear Magnetic Resonance (NMR) Spectroscopy

A Bruker Ultrashield 500 plus NMR spectrometer was used to measure the proton and carbon chemical shifts. The proton and carbon chemical shifts are listed referenced to TMS. Integration of the proton resonance frequency absorption defined the number of protons observed. Proton and carbon chemical shifts and integration of the proton peaks were used to identify the material product.

Preparatory Example 1 (PE-1), 4-S-(5-methyl-1,3,4-thiadiazole-2-mercapto)phthalonitrile 4-nitrophthalonitrile (10.00 g) and 5-methyl-2-mercapto-1,3,4-thiadiazole (7.64 g) were added to a 250 mL round bottom flask. 70 g of DMSO was added to the flask. The 4-nitrophthalonitrile and the 5-methyl-2-mercapto-1,3,4-thiadiazole were dissolved in the DMSO by stirring with an egg-shaped stir bar on a magnetic stir plate. Potassium carbonate (10.00 g) was added in one addition. The solution was stirred with an egg-shaped stir bar. A slow nitrogen purge was applied to the vessel and vented through a needle in a rubber septum. After 16 hours, the DMSO solution was decanted from the undissolved salts and slowly poured into a 2× volume of stirring cold 70/30 (by mass) methanol/water solution. A solid crystallized from the solution. The solids were collected on a Buchner funnel with suction and washed with cold 70/30 methanol/water. The solids were air dried overnight. The solids were greyish-white in color. The total amount of solids collected was 3.88 g (26% yield). The solids had a melt temperature of 141.9° C. as measured by differential scanning calorimetry, and were identified as 4-S-(5-methyl-1,3,4-thiadiazole-2-mercapto)phthalonitrile by infrared and NMR analysis.

DSC $T_m$=141.9° C. FTIR (ATR; cm$^{-1}$): 2233 (—CN), 1584 (C=C aromatic), 1550 (C=N), 656 (C—S), 627 (C—S). $^1$H NMR (500 MHz, Acetone; δ, ppm): 8.226 (s, 1H), 8.119 (d, 1H), 8.036 (d, 1H), 2.824 (s, 3H). $^{13}$C NMR (500 MHz, Acetone; δ, ppm): 170.61, 160.01, 141.69, 135.40, 135.07, 134.91, 117.48, 116.10, 115.74, 115.39, 15.88.

Preparatory Example 2 (PE-2), 4-S-(5-methyl-1,3,4-thiadiazole-2-mercapto)phthalonitrile 4-nitrophthalonitrile (4.00 g), 5-methyl-2-mercapto-1,3,4-thiadiazole (3.05 g) and potassium carbonate (4.00 g) were added to a 40 mL glass vial with a magnetic stir bar. 25 g of DMF was added to the vial and the vial was sealed. The contents of the vial were stirred on a magnetic stir plate at ambient temperature overnight for 16 hours. The next day, the solution was added to a 2× volume of cold methanol/water (60/40 by mass), which caused product separation. More ice was directly added to the stirring solution, which caused more solid separation. The solid, 3.8 g (67.3% yield), was collected and washed with water and cold methanol/water (60/40). The solids were removed from the Buchner funnel and dried in an oven set at 120° C. The solids were orange in color. The solid was identified as 4-S-(5-methyl-1,3,4-thiadiazole-2-mercapto)phthalonitrile by infrared and NMR analysis.

Example 1 (EX-1), 4-S-(5-amino-1,3,4-thiadiazole-2-mercapto)phthalonitrile (i.e., ATTPN)

4-nitrophthalonitrile (100.00 g) and 5-amino-2-mercapto-1,3,4-thiadiazole (76.95 g) were weighed into a 3 L round bottom flask. 500 g of DMSO was added. The flask was fitted with a polytetrafluoroethylene (PTFE) stir blade and stir rod and mechanically mixed to dissolve the 4-nitrophthalonitrile and 5-amino-2-mercapto-1,3,4-thiadiazole. 120 mL of triethylamine was added in one addition. The flask necks were sealed with rubber septa other than the stir rod shaft and fitted with a thermoprobe inserted through one of the rubber septa. The flask solution was mechanically stirred and heated to 70° C. Upon heating to 70° C., the solution generated an exotherm and superheated to 75° C. The temperature equilibrated at 70° C. within 30 min. The flask solution was stirred for an additional 2 hours and 30 min at 70° C. After three hours, the solution was added to 1000 mL of ice water stirring with a mechanical mixer. The separated solid was collected on a Buchner funnel on filter paper and washed with water. The collected solid was placed in an aluminum pan and dried in a convection oven set at 120° C. The dried solid was placed in a 2000 mL beaker and 400 mL of dichloromethane was added to the beaker. The solution was mechanically stirred. After 30 min, the undissolved solids were collected on a Buchner funnel with suction. The solids were washed with dichloromethane. The solid was removed from the Buchner funnel and air dried in an aluminum pan overnight. The solid was orange in color. The total amount of solids collected was 102.9 g (68.7% yield). The solids had a melt temperature of 184.6° C. as measured by differential scanning calorimetry, and were identified as 4-S-(5-amino-1,3,4-thiadiazole-2-mercapto)phthalonitrile by infrared and NMR analysis. DSC $T_m$=184.6° C. FTIR (ATR; cm$^{-1}$): 2224 (—CN), 1580 (C=C aromatic), 1550 (C=N), 669 (C—S), 638 (C—S). $^1$H NMR (500 MHz, DMSO; δ, ppm): 8.115 (d, 1H), 8.080 (d, 1H), 7.865 (s, 2H), 7.677 (m, 1H). $^{13}$C NMR (500 MHz, DMSO; δ, ppm): 173.20, 143.31, 141.85, 134.53, 131.43, 131.30, 115.75, 115.61, 115.32, 112.32.

Example 2 (EX-2), ATTPN 4-nitrophthalonitrile (45.00 g) and 5-amino-2-mercapto-1,3,4-thiadiazole (34.63 g) were added to a 500 mL round bottom flask. 250 g of DMSO was added to the flask. The 4-nitrophthalonitrile and the 5-amino-2-mercapto-1,3,4-thiadiazole were dissolved in the DMSO by stirring with an egg-shaped stir bar on a magnetic stir plate. Potassium carbonate (44.90 g) was added in one addition. The solution was stirred with an egg shaped stir bar. After 1.5 hours, the DMSO solution transitioned to a viscous sludge. The sludge was broken up with a spatula, and was removed from the flask. The sludge was added to a 500 mL of stirring ice water, which produced a precipitate. The precipitate was collected on a Buchner funnel and washed with water and with 60/40 cold methanol/water. The collected solids were air dried overnight and dried in an oven set at 120° C. the next day for 1 hour. The solids were orange in color. The solids, 29.4 g (44% yield), were identified as 4-S-(5-amino-1,3,4-thiadiazole-2-mercapto)phthalonitrile by infrared and NMR analysis.

Example 3 (EX-3), ATTPN 4-nitrophthalonitrile (4.00 g), 5-amino-2-mercapto-1,3,4-thiadiazole (3.08 g) and potassium carbonate (4.00 g) were added to a 40 mL glass vial with a magnetic stir bar. 25 g of DMF was added to the vial and the vial was sealed. The contents of the vial were stirred on a magnetic stir plate at ambient temperature overnight for 16 hours. The next day, the solution was added to a 2× volume of cold methanol/water (60/40 by mass), which caused product separation. More ice was directly added to the stirring solution, which caused more solid separation. The solids were collected and washed with water and cold methanol/water (60/40). The solids were removed from the Buchner funnel and dried in an oven at 120° C. The solids were orange in color. The solid, 4.10 g (68.4% yield), was identified as 4-S-(5-amino-1,3,4-thiadiazole-2-mercapto)phthalonitrile by infrared and NMR analysis.

Example 4 (EX-4), 4-S-(1,3,4-thiadiazole-2-mercapto)phthalonitrile 4-nitrophthalonitrile (4.00 g), 2-mercapto-1,3,4-thiadiazole (2.73 g) were added to a 40 mL glass vial with a magnetic stir bar. 25 g of DMF was added to the vial and the solids in the vial were dissolved with stirring. Potassium carbonate (4.00 g) and 3 Å molecular sieves (2.0 g) were added to the vial, and the vial was sealed. The contents of the vial were stirred on a magnetic stir plate at ambient temperature for 48 hours. The solution was decanted off of the salts and molecular sieves and added to a 4× volume of cold methanol/water (60/40 by mass) which caused product separation. The solution sat overnight without agitation to allow further crystallization. The solids were collected on a Buchner funnel with suction and washed with cold methanol/water (60/40) and water. The solids were removed from the Buchner funnel and dried in an oven set at 120° C. The solids were white cream in color. The total amount of solids collected was 3.83 g (68% yield). The solid was identified as 4-S-(1,3,4-thiadiazole-2-mercapto)phthalonitrile by infrared and NMR analysis.

FTIR (ATR; cm$^{-1}$): 2233 (—CN), 1581 (C=C aromatic), 1545 (C=N), 656 (C—S), 601 (C—S). $^1$H NMR (500 MHz, DMSO; δ, ppm): 9.777 (s, 1H), 8.417 (d, 1H), 8.181 (d, 1H), 8.033 (quad, 1H). $^{13}$C NMR (500 MHz, DMSO; δ, ppm): 160.91, 157.75, 139.61, 135.20, 135.01, 134.72, 115.82, 115.57, 115.18, 114.10.

Example 5 (EX-5), 4-S-(5-methylmercapto-1,3,4-thiadiazole-2-mercapto)phthalonitrile (i.e., MTTTPN)

4-nitrophthalonitrile (4.00 g), 5-methylmercapto-2-mercapto-1,3,4-thiadiazole (3.79 g) were added to a 40 mL glass vial with a magnetic stir bar. 25 g of DMF was added to the vial and the solids in the vial were dissolved with stirring. Potassium carbonate (4.00 g) and 3 Å molecular sieves (2.0 g) were added to the vial, and the vial was sealed. The contents of the vial were stirred on a magnetic stir plate at ambient temperature for 48 hours. The solution was decanted off of the salts and molecular sieves and added to a 4× volume of cold ethanol/water (60/40 by mass), which caused product separation. The solution sat overnight without agitation to allow further crystallization. The solids were collected on a Buchner funnel with suction and washed with cold ethanol and water. The solids were removed from the Buchner funnel and dried in an oven set at 120° C. The solids were white cream in color. The total amount of solids collected was 4.70 g (70% yield). The solid was identified as 4-S-(5-methylmercapto-1,3,4-thiadiazole-2-mercapto) phthalonitrile by infrared and NMR analysis.

FTIR (ATR; cm$^{-1}$): 2226 (—CN), 1582 (C=C aromatic), 1547 (C=N), 651 (C—S), 594 (C—S) 2233 (—CN), 1581 (C=C aromatic), 1545 (C=N), 656 (C—S), 601 (C—S). $^1$H NMR (500 MHz, DMSO; δ, ppm): 8.344 (d, 1H), 8.150 (d, 1H), 7.950 (quad, 1H), 2.793 (s, 3H). $^{13}$C NMR (500 MHz, DMSO; δ, ppm): 172.19, 158.08, 140.39, 134.67, 134.07, 133.96, 115.82, 115.59, 115.20, 113.75, 16.43.

Example 6 (EX-6), ATTPN 4-nitrophthalonitrile (100.00 g) and 5-amino-2-mercapto-1,3,4-thiadiazole (76.95 g) were weighed into a three neck 3 L round bottom flask. 500 g of DMSO was added. The flask was fitted with nitrogen gas purge line and with a PTFE stir blade and stir rod. The flask was purged with a continuous nitrogen gas flow. The DMSO solution was mechanically mixed to dissolve the 4-nitrophthalonitrile and 5-amino-2-mercapto-1,3,4-thiadiazole. After all solids had dissolved in the DMSO, 15 g of 3 Å molecular sieves and 100 mL of triethylamine were added in two separate additions. The flask was purged with nitrogen gas for several more minutes. The nitrogen gas purge line was closed. The open flask neck for the nitrogen purge was sealed with a rubber septum. The flask solution was mechanically stirred for 24 hours at ambient temperature. At the end of 24 hours, a solid had crystallized out of solution. The solution and crystalline solid were decanted from the flask, leaving the molecular sieves in the flask, and added to 1000 mL of ice water stirring with a mechanical mixer. The separated solid was collected on filter paper using a Buchner funnel with suction and washed with water. The collected solid was placed in an aluminum pan and dried in a convection oven set at 120° C. for 4 hours. The dried solid was placed in a 2000 mL beaker and 600 mL of dichloromethane was added to the beaker. The solution was mechanically stirred for 1 hour. The solids were collected on filter paper using a Buchner funnel with suction and washed with dichloromethane. The solids were removed from the Buchner funnel and air dried in an aluminum pan overnight. The solid was orange in color. The total amount of solids collected was 121.9 g (81.4% yield). The solids had a melt temperature of 184.6° C. as measured by differential scanning calorimetry, and were identified as 4-S-(5-amino-1,3,4-thiadiazole-2-mercapto)phthalonitrile by infrared and NMR analysis.

DSC $T_m$=184.6° C. FTIR (ATR; cm$^{-1}$): 2224 (—CN), 1580 (C=C aromatic), 1550 (C=N), 669 (C—S), 638 (C—S). $^1$H NMR (500 MHz, DMSO; δ, ppm): 8.115 (d, 1H), 8.080 (d, 1H), 7.865 (s, 2H), 7.677 (m, 1H). $^{13}$C NMR (500 MHz, DMSO; δ, ppm): 173.20, 143.31, 141.85, 134.53, 131.43, 131.30, 115.75, 115.61, 115.32, 112.32.

Example 7 (EX-7)

10.0 g of ATTPN from EX-6 was weighed into a flat bottom 70 mm diameter thin gauge aluminum pan. The ATTPN was placed on a hot plate at 190° C. The ATTPN melted to a liquid. Upon melting, the ATTPN generated an exotherm and underwent a thermosetting polymerization reaction to a solid. The polymerized resin was post-cured at 280° C. and generated a second exotherm where the glass transition temperature of the polymerized resin increased to 319° C., as measured by DSC. The two exotherms were measured by DSC with a heating rate of 1° C./min. The first exotherm had a peak temperature of 197° C. The second exotherm had a peak temperature of 279° C.

Example 8 (EX-8)

6.86 g of BMPN was melted at a temperature of 175° C. in a flat bottom 70 mm diameter thin gauge aluminum pan. 1.14 g of ATTPN from EX-6 was added and dissolved into the BMPN with stirring. The resin blend was degassed for 30 min in a vacuum oven set at 175° C. to remove entrapped air. The resin was placed in an air circulating oven and polymerized 4 hours at 200° C., 4 hours at 250° C., and 4 hours at 300° C., ramping 3° C./min between set points. The monomer resin underwent a thermosetting network polymerization to a hard stiff solid. The solid was cooled at 5° C./min to 40° C. and removed from the aluminum pan. The sample was cut into strips for DMA measurement of the stiffness (E') in megapascals (MPa), softening temperature (E'(onset)), and glass transition temperature (tan δ peak) in single cantilever beam geometry. The data for EX-8 is provided in Table 2 below.

Example 9 (EX-9)

6.86 g of BTPN was melted at a temperature of 175° C. in a flat bottom 70 mm diameter thin gauge aluminum pan. 1.14 g of ATTPN from EX-6 was added and dissolved into the BTPN with stirring. The resin blend was degassed for 30 min in a vacuum oven set at 175° C. to remove entrapped air. The resin was placed in an air circulating oven and polymerized 4 hours at 200° C., 4 hours at 250° C., and 4 hours at 300° C., ramping 3° C./min between set points. The monomer resin underwent a thermosetting network polymerization to a hard stiff solid. The solid was cooled at 5° C./min to 40° C. and removed from the aluminum pan. The sample was cut into strips for DMA measurement of the stiffness (E'), softening temperature (E'(onset)), and glass transition temperature (tan δ peak) in single cantilever beam geometry. The data for EX-9 is provided in Table 2 below.

TABLE 2

DMA measurements of ATTPN resin blends

| | Resin Blend | DMA (cantilever, 3° C./min ramp) | | |
|---|---|---|---|---|
| Example | Composition | Mass % ATTPN | E' (25° C.) [MPa] | $T_g$ (E' onset) [° C.] | $T_g$ (tan d peak) [° C.] |
| EX-8 | BMPN/ATTPN | 14 | 3100 | 181 | 224 |
| EX-9 | BTPN/ATTPN | 14 | 3150 | 203 | 277 |

Example 10 (EX-10)

6.00 g of BTPN was melted at a temperature of 175° C. in a flat bottom 70 mm diameter thin gauge aluminum pan. 2.00 g of 4-S-(5-methylmercapto-1,3,4-thiadiazole-2-mercapto)phthalonitrile (MTTTPN) from EX-5 was added and dissolved into the BTPN with stirring. 0.333 g of 4,4'-(1,3-phenylenedioxy)dianiline was added to the resin blend and dissolved with stirring. The resin blend was degassed for 30 min in a vacuum oven set at 175° C. to remove entrapped air. The resin was placed in an air circulating oven and polymerized 4 hours at 200° C., 4 hours at 250° C., and 4 hours at 300° C., ramping 3° C./min between set points. The monomer resin underwent a thermosetting network polymerization to a hard stiff solid. The solid was cooled at 5° C./min to 40° C. and removed from the aluminum pan. The sample was cut into strips for DMA measurement of the stiffness (E'), softening temperature (E'(onset)), and glass transition temperature (tan δ peak) in single cantilever beam geometry. The data for EX-10 is provided in Table 3 below.

TABLE 3

DMA measurements of MTTTPN resin blends

| | Resin Blend | DMA (cantilever, 3° C./min ramp) | | |
|---|---|---|---|---|
| Example | Composition | Mass % MTTTPN | E'(25° C.) [MPa] | $T_g$ (E' onset) [° C.] | $T_g$ (tan d peak) [° C.] |
| EX-10 | BTPN/MTTTPN | 20 | 3200 | 346 | 386 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A resin blend comprising at least one phthalonitrile resin and a compound of Formula I:

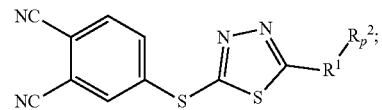

wherein p is 0 or 1;
when p is 0, $R^1$ is H, an alkyl group, an aryl group, a heteroalkyl group, a heteroaryl group, a thienyl group, an alkoxy group, an alkoxycarbonyl group, an alkylcarbonyl group, a hydroxyl group, a thiol group, an amino group, —CH(=O), —S—$R^3$, —C(=O)—N—$R_2^4$, —S($O_2$)—$R^5$, a carboxylic acid group, or a halogen, wherein $R^3$ is an alkyl group, each $R^4$ is independently H or an alkyl group and $R^5$ is H or an alkyl group; and
when p is 1, $R^1$ is a covalent bond, an arylene group, or an aralkylene group, and $R^2$ is an alkyl group, an aryl group, a heteroalkyl group, a heteroaryl group, a thienyl group, an alkoxy group, an alkoxycarbonyl group an alkylcarbonyl group, a hydroxyl group, a thiol group, an amino group, —CH(=O), —S—$R^3$, —C(=O)—N—$R_2^4$, —S($O_2$)—$R^5$, a carboxylic acid group, or a halogen, wherein $R^3$ is an alkyl group, each $R^4$ is independently H or an alkyl group, and $R^5$ is H or an alkyl group.

2. The resin blend of claim 1, wherein p is 0 and $R^1$ is H, an alkyl group, a heteroalkyl group, or an amino group.

3. The resin blend of claim 1, wherein the at least one phthalonitrile resin is selected from bis(3,4-dicyanophenyl) ether of resorcinol, bis(3,4-dicyanophenyl) ether of bisphenol A, bis(3,4-dicyanophenyl) ether of bisphenol M, bis(3, 4-dicyanophenyl) ether of bisphenol P, bis(3,4-dicyanophenyl) ether of bisphenol T, or a combination thereof.

4. The resin blend of claim 1, wherein the compound of Formula I is present in an amount of 1 to 70 weight percent (wt. %), based on the total weight of the at least one phthalonitrile resin.

5. The resin blend of claim 1, further comprising at least one additive selected from a toughener, a filler, or a combination thereof.

6. The resin blend of claim 5, wherein the filler comprises particles of a metal carbide, a metal oxide, silica, carbon, a metal carbonate, a metal nitride, a metal hydroxide, a metal sulfate, barium titanate, glass bubbles, cenospheres, or a combination thereof.

7. An article comprising a polymerization product of the resin blend of claim 1.

8. A compound of Formula II:

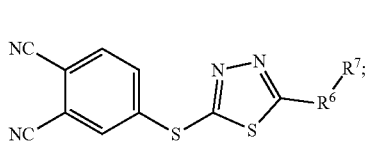

II wherein $R^6$ is a covalent bond, an arylene group, or an aralkylene group, and $R^7$ is a hydroxyl group, a thiol group, —S—$R^8$, wherein $R^8$ is an alkyl group, or an amino group.

9. The compound of claim 8, wherein $R^6$ is a covalent bond.

10. The compound of claim 8, wherein $R^7$ is an amino group.

11. An article comprising a polymerized reaction product of the compound of Formula II of claim 8.

12. A method of making a compound of Formula II:

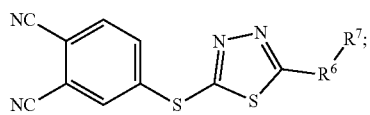

II wherein $R^6$ is a covalent bond, an arylene group, or an aralkylene group, and $R^7$ is a hydroxyl group, a thiol group, —S—$R^8$, wherein $R^8$ is an alkyl group, or an amino group, the method comprising:
a) combining components to form a mixture, the components comprising:
  i) 4-nitrophthalonitrile;
  ii) a compound of Formula III:

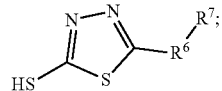

III wherein $R^6$ and $R^7$ are as defined for Formula II;
  iii) an aprotic solvent; and
  iv) a base; and
b) reacting the mixture with stirring.

13. The method of claim 12, further comprising cooling the mixture.

14. The method of claim 12, further comprising adding molecular sieves to the reaction mixture.

15. The method of claim 12, further comprising precipitating the compound of Formula II from the reaction mixture in a blend of water and alcohol.

* * * * *